(12) United States Patent
Rem-Bronneberg

(10) Patent No.: US 10,772,655 B2
(45) Date of Patent: Sep. 15, 2020

(54) ULTRASOUND ABLATION DEVICE

(71) Applicant: KONINKLIJKE PHILIPS N.V., Eindhoven (NL)

(72) Inventor: Debbie Rem-Bronneberg, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 212 days.

(21) Appl. No.: 16/079,127

(22) PCT Filed: Feb. 10, 2017

(86) PCT No.: PCT/EP2017/052962
§ 371 (c)(1),
(2) Date: Aug. 23, 2018

(87) PCT Pub. No.: WO2017/144288
PCT Pub. Date: Aug. 31, 2017

(65) Prior Publication Data
US 2019/0053821 A1    Feb. 21, 2019

(30) Foreign Application Priority Data

Feb. 23, 2016    (EP) .................................... 16156977

(51) Int. Cl.
*A61B 17/32*    (2006.01)
*A61N 7/02*    (2006.01)
(Continued)

(52) U.S. Cl.
CPC ................ *A61B 17/320068* (2013.01); *A61B 17/320016* (2013.01); *A61N 7/02* (2013.01);
(Continued)

(58) Field of Classification Search
CPC .............. A61N 7/02; A61N 2007/0047; A61N 2007/0078; A61N 2007/025;
(Continued)

(56) References Cited

U.S. PATENT DOCUMENTS 6,086,581  A      7/2000  Reynolds
6,626,855  B1 *   9/2003  Weng ........................ A61B 8/12
                                                          600/439
(Continued)

FOREIGN PATENT DOCUMENTS

WO    2002096501 A2    12/2002
WO    2004108214 A1    12/2004
(Continued)

*Primary Examiner* — Phong Son H Dang

(57) ABSTRACT

The invention relates to an interstitial ultrasound ablation device (5) for being inserted into tissue surrounding, for instance, a tumor. The interstitial ultrasound ablation device comprises an arrangement (7) of ultrasound units (17, 18) for a focal ablation treatment which is modifiable from a folded configuration, to be used while inserting the ultrasound ablation device into the tissue, to an unfolded configuration, to be used after the ultrasound ablation device has been inserted into the tissue, such that the unfolded arrangement of ultrasound units is next to the tumor. This ultrasound ablation device can be easily positioned close to the tumor, where the unfolded arrangement of ultrasound units provides a large ultrasound emission area allowing for a very good focusing of the ultrasound on the tumor. This can lead to a very effective ablation of the tumor with only very few or no unwanted side effects.

12 Claims, 6 Drawing Sheets

(51) Int. Cl.
    *A61B 17/00*     (2006.01)
    *A61N 7/00*     (2006.01)

(52) U.S. Cl.
    CPC .............. *A61B 2017/00274* (2013.01); *A61B 2017/320069* (2017.08); *A61N 2007/0047* (2013.01); *A61N 2007/0078* (2013.01); *A61N 2007/025* (2013.01)

(58) Field of Classification Search
    CPC .... A61B 17/320068; A61B 17/320016; A61B 2017/320069; A61B 2017/00274
    See application file for complete search history.

(56) References Cited

U.S. PATENT DOCUMENTS

| | | | |
|---|---|---|---|
| 6,669,693 B2 | 12/2003 | Friedman | |
| 7,285,120 B2 | 10/2007 | Im | |
| 7,473,224 B2 * | 1/2009 | Makin | A61B 8/12 600/439 |
| 8,057,391 B2 * | 11/2011 | Lau | A61B 8/12 600/439 |
| 8,277,379 B2 * | 10/2012 | Lau | A61N 7/022 600/439 |
| 8,709,008 B2 * | 4/2014 | Willis | A61B 18/1492 606/41 |
| 8,939,970 B2 * | 1/2015 | Stone | A61B 18/1492 606/41 |
| 8,951,251 B2 * | 2/2015 | Willard | A61N 7/022 606/41 |
| 9,125,666 B2 * | 9/2015 | Steinke | A61B 18/1492 |
| 9,770,606 B2 * | 9/2017 | Pikus | A61N 7/022 |
| 10,070,772 B2 * | 9/2018 | Peh | A61B 1/015 |
| 10,265,122 B2 * | 4/2019 | Wang | A61B 18/1492 |
| 2004/0242999 A1 * | 12/2004 | Vitek | A61B 17/2202 600/437 |
| 2007/0185554 A1 | 8/2007 | Appling | |
| 2007/0239011 A1 | 10/2007 | Lau | |
| 2010/0228239 A1 | 9/2010 | Freed | |
| 2012/0310226 A1 | 12/2012 | Fourkas | |
| 2013/0096550 A1 * | 4/2013 | Hill | A61B 18/1492 606/33 |
| 2013/0178738 A1 | 7/2013 | Martin | |
| 2014/0081301 A1 | 3/2014 | Tran | |
| 2014/0207001 A1 | 7/2014 | Seo | |
| 2014/0276781 A1 | 9/2014 | Beani | |
| 2014/0330124 A1 | 11/2014 | Carol | |

FOREIGN PATENT DOCUMENTS

| | | |
|---|---|---|
| WO | 2012054762 A2 | 4/2012 |
| WO | 2013157207 A1 | 10/2013 |

\* cited by examiner

ULTRASOUND ABLATION DEVICE

CROSS-REFERENCE TO PRIOR APPLICATIONS

This application is the U.S. National Phase application under 35 U.S.C. § 371 of International Application No. PCT/EP2017/052962, filed on Feb. 10, 2017, which claims the benefit of European Patent Application No. 16156977.7, filed on Feb. 23, 2016. These applications are hereby incorporated by reference herein.

FIELD OF THE INVENTION

The invention relates to an ultrasound ablation device for a focal ablation treatment of an object like a tumor within a subject. The invention further relates to an ultrasound ablation system comprising the ultrasound ablation device. Moreover, the invention relates to an ultrasound ablation method and computer program for a focal ablation treatment of an object within a subject.

BACKGROUND OF THE INVENTION

WO 2002/096501 A2 discloses an ultrasound medical system comprising an ultrasound transducer assembly insertable into a patient, wherein the ultrasound transducer assembly has a longitudinal axis and a plurality P of ultrasound transducers. Each ultrasound transducer has an ultrasound emission surface oriented at an angle of substantially 360/P degrees apart from the ultrasound emission surface of an adjacent ultrasound transducer when viewed in a cross section of the ultrasound transducer assembly taken by a cutting plane which is perpendicular to the longitudinal axis.

US 2004/0242999 A1 discloses an apparatus for delivering acoustic energy to a target site adjacent a body passage. The apparatus comprises a first member with a proximal end, a distal end having a size and shape for insertion into the body passage, and a first transducer carried on the distal end. The apparatus further comprises a second member with a proximal end, a distal end having a size and shape for insertion into the body passage, and a second transducer carried on the distal end. The first and second transducers are detachably coupled to each other to at least partially form a transducer array for delivering acoustic energy to a target site adjacent the body passage.

US 2014/0330124 A1 discloses a system for providing ultrasound, wherein the system comprises a drive shaft having a proximal end and a distal end, a motor positioned at or near the proximal end of the drive shaft and a pair of jaws mounted on or near the distal end of the drive shaft. The system further comprises ultrasound transducers configured to generate thermal or cavitational lesions with ultrasound, wherein each transducer is mounted to one of the jaws.

US 2007/0239011 A1 discloses an apparatus for delivering high intensity focused ultrasound (HIFU) energy to a treatment site internal to a patient's body. The apparatus comprises an elongate probe having a proximal end and a distal end, wherein the proximal end has a section adapted for positioning the distal end of the probe at a desired location within the patient's body. The distal end of the probe has a HIFU therapy transducer coupled thereto, wherein the HIFU therapy transducer comprises a plurality of leaves, each leaf having a proximal end, a distal end, and a deployment mechanism, wherein the proximal end of each leaf is coupled to the distal end of the probe. Each leaf further has a front surface adapted to direct HIFU energy to the treatment site when the probe is inserted in the patient's body and the deployment mechanism is activated. The deployment mechanism is configured to deploy the leaves by directing the distal end of the leaves in a radially outward direction, wherein the leaves thus deployed collectively provide a bowl-shaped HIFU therapy transducer having an outer edge with a diameter that is larger than the diameter of the probe and an aperture of a size sufficient to direct therapeutic HIFU energy to the treatment site. In order to facilitate insertion of the probe in the patient's body, the leaves are configured to collapse when the deployment mechanism is not activated, wherein the collapsed leaves occupy a space having a diameter smaller than the diameter of the outer edge of the HIFU therapy transducer.

US 2014/0081301 A1 discloses an intravascular nerve modulation system comprising an elongate shaft having a proximal end region and a distal end region and an array of ultrasound ablation transducers disposed at the distal end region. Each of the ablation transducers in the array is configured to emit acoustic energy directed towards and intersecting at a first focal region.

WO 2004/108214 A1 discloses an ultrasound probe comprising a probe body and a transducer means for generating a focused ultrasound field, wherein the intensity maximum of which is located in an object for heating the same. The transducer means has a central opening formed by one or more holes for reducing the effect of unwanted peaks in the near ultrasound field.

For ablating a tumor in the prostate it is known to use a transrectal HIFU ablation device. Using the transrectal HIFU ablation device for ablating a tumor in the prostate can lead to unwanted side effects like adversely affecting the urethra, the nerves or the rectum. The side effects can lead to incontinence and erectile dysfunction.

SUMMARY OF THE INVENTION

It is an object of the present invention to provide an ultrasound ablation device which allows for an improved focal ablation treatment of an object within a subject, especially to a focal ablation treatment having fewer or no unwanted side effects. It is a further object of the present invention to provide an ultrasound ablation system comprising the ultrasound ablation device. Moreover, it is an object of the present invention to provide an ultrasound ablation method and computer program for a focal ablation treatment of an object within a subject.

In a first aspect of the present invention an ultrasound ablation device for a focal ablation treatment of an object within a subject is presented, wherein the ultrasound ablation device is an interstitial device to be inserted into tissue surrounding the object and comprises an arrangement of ultrasound units for focally ablating the object by ultrasound, wherein the arrangement of ultrasound units is modifiable from a folded configuration, to be used while inserting the ultrasound ablation device into the tissue, to an unfolded configuration, to be used after the ultrasound ablation device has been inserted into the tissue, such that the unfolded arrangement of ultrasound units is next to the object, wherein the ultrasound ablation device comprises an inflatable balloon for creating space within the tissue by inflating the balloon, wherein each ultrasound unit comprises an ultrasound emission surface, wherein the arrangement of ultrasound units is located on a surface of the inflatable balloon such that in the unfolded configuration the ultrasound emission surfaces are directed towards the inside of the balloon.

Since the ultrasound ablation device is an interstitial ultrasound ablation device, which is adapted to be inserted into tissue surrounding the object, the ultrasound ablation device can be positioned relatively close to the object to be treated. Moreover, this positioning of the ultrasound ablation device close to the object can be carried out relatively easily, because during the insertion of the ultrasound ablation device into the tissue surrounding the object the folded and hence smaller configuration of the arrangement of ultrasound units can be used. After the ultrasound ablation device has been inserted into the tissue surrounding the object, the arrangement of ultrasound units can be unfolded such that it provides a relatively large ultrasound emission area next to and partly surrounding the object. This relatively large ultrasound emission area next to and surrounding the object allows for a very good focusing of the ultrasound on the object, thereby allowing for a very effective ablation of the object with fewer or no unwanted side effects.

The object is preferentially a tumor like a tumor in the prostate or in another organ like the liver. The ultrasound ablation device is preferentially a needle. However, it can also be another interventional device like a catheter, an endoscope, et cetera. The ultrasound units preferentially comprise capacitive micromachined ultrasound transducers (CMUT). However, the ultrasound units can also comprise other types of ultrasound transducers like ceramic lead zirconate titanate (PZT) or single crystal ultrasound transducers.

In an embodiment the arrangement of ultrasound units is adapted such that in the folded configuration the ultrasound emission surfaces of at least some of the ultrasound units face each other and that, while unfolding the arrangement of ultrasound units, these ultrasound units are folded back so that first ends of these ultrasound units move away from each other and opposing second ends of these ultrasound units do not move away from each other. The ultrasound units may further include a base ultrasound unit being surrounded by the second ends of the ultrasound units that are folded back while unfolding the arrangement. This arrangement of ultrasound units may be regarded as being flower-like, wherein the ultrasound units that are folded back correspond to flower petals and the unfolding can be regarded as corresponding to an opening of the flower petals. In its unfolded configuration the object can very effectively be ablated by using the ultrasound emission surfaces of the ultrasound units.

The base ultrasound unit preferentially has an opening for allowing a fluid to traverse the base ultrasound unit. For instance, the opening can be used for allowing cooling fluid to traverse the base element, in order to cool the ultrasound units. The opening can also be used to allow fluid for filtering the ultrasound near field to pass the base element. This can further reduce unwanted side effects. The same fluid may be used for different purposes, for instance, for cooling and for filtering the ultrasound near field. The opening may be centrally located in the base ultrasound unit. Moreover, the base ultrasound unit may be circular. The ultrasound units, which correspond to the flower petals, may be longish elements. They may be rectangular. However, they can also have another shape. For instance, they can be triangular. Moreover, they can be identical, or at least two of the ultrasound units, which correspond to the flower petals, can be different to each other. These ultrasound units can be different, in order to optimize an ultrasound focus region which should be used for ablating the object. This can lead to a further improved ultrasound ablation device.

It is preferred that the ultrasound ablation device comprises an inner space for accommodating the arrangement of ultrasound units in its folded configuration, wherein the arrangement of ultrasound units and the inner space are movable relatively to each other for moving the arrangement of ultrasound units out of the inner space into the tissue where the arrangement of ultrasound units is unfoldable. The inner space can be used for holding the arrangement in its folded configuration and/or for protecting the arrangement while being introduced into the tissue. For instance, the ultrasound ablation device can comprise a shaft to be inserted into the tissue surrounding the object, wherein the shaft may comprise an inner space for accommodating the arrangement of ultrasound units in its folded configuration. For unfolding the arrangement of ultrasound units the arrangement of ultrasound units may be moved out of the inner space into the tissue. The ultrasound ablation device can also comprise a sheath, wherein the arrangement of ultrasound units may be located within the sheath in its folded configuration, wherein for unfolding the arrangement of ultrasound units the sheath may be removed from the arrangement of ultrasound units. In this case the inner space is the space within the sheath.

The ultrasound ablation device, i.e. the arrangement of ultrasound units in its unfolded configuration, can be forward-looking. Preferentially, the arrangement of ultrasound units is located at a distal tip of an elongated shaft of a needle, a catheter, an endoscope or another elongated device, wherein the term "forward" refers to the direction of the movement of the tip into the tissue. The arrangement of ultrasound units can also be sideward-looking. Also in this case the arrangement of ultrasound units is preferentially located at a shaft of an elongated device, wherein the term "sideward" refers to an ultrasound emission direction being substantially transversal, especially orthogonal, to the longitudinal axis of the elongated device. An arrangement of ultrasound units, which is sideward-looking in its unfolded configuration, may surround the shaft of the elongated device in its folded configuration. In particular, in its folded configuration the arrangement of ultrasound units may surround the shaft, wherein the arrangement may be held in the folded configuration by a sheath, which surrounds the shafts and the arrangement of ultrasound units. For unfolding the arrangement of ultrasound units the sheath may be retracted from the shaft.

The ultrasound ablation device comprises an inflatable balloon for creating space within the tissue by inflating the balloon. The arrangement of ultrasound units can be located within the inflatable balloon. However, the arrangement of ultrasound units can also be located outside the inflatable balloon. The arrangement of ultrasound units is located on a surface of an inflatable balloon, with a distance to the surface or with contact to the surface, wherein the arrangement of the ultrasound units is modified from the folded configuration to the unfolded configuration by inflating the balloon. The ultrasound units can be located on an inner surface or on an outer surface of the balloon. It is also possible that one or more ultrasound units are located on the inner surface and one or more ultrasound units are located on the outer surface. By inflating the balloon the ultrasound units can be pushed or pulled, depending on whether they are arranged on the inner surface or the outer surface, such that the arrangement of ultrasound units is unfolded. Also this leads to an unfolding of the arrangement of ultrasound units in a relatively simple way. For inflating the balloon a fluid is used, wherein the fluid for inflating the balloon can also be used for cooling the ultrasound units and/or for filtering the ultrasound near field. Moreover, the inflated balloon can act as a lens further focusing the ultrasound, which can result in a further improved confinement of the ultrasound focus region. This can lead to a further reduced likelihood of unwanted side effects. The arrangement of ultrasound units and the balloon are adapted to generate an ultrasound focus outside the balloon, if the balloon is inflated.

That the ultrasound emission surfaces are directed towards the inside of the balloon means that the ultrasound units are located on the surface of the inflatable balloon such that ultrasound radiation, which is emitted by the ultrasound emission surfaces, travels through the inside of the balloon. In an embodiment the arrangement of ultrasound units is located on an outer surface of the inflatable balloon such that the ultrasound emission surfaces face the outer surface of the inflatable balloon. Moreover, in an embodiment each ultrasound unit comprises a respective non-ultrasound-emission surface being opposite to the respective ultrasound emission surface, wherein the arrangement of ultrasound units is located on an inner surface of the inflatable balloon such that the non-ultrasound-emission surfaces face the inner surface of the inflatable balloon. If the ultrasound emission surfaces define front surfaces of the ultrasound units, the non-ultrasound-emission surfaces may define back surfaces of the ultrasound units.

The ultrasound ablation device can comprise a shaft to be inserted into the tissue surrounding the object, wherein the arrangement of ultrasound units can be arranged at, and rotatably relative to, the shaft. This allows for a change of the location of the ultrasound focus region without requiring a rotation of the entire shaft. This can further improve the handling of the ultrasound ablation device such that the ultrasound focus region covers the object to be ablated.

The ultrasound ablation device can comprise a sensor for sensing the degree of unfolding of the arrangement of ultrasound units. The sensor can be, for instance, a strain sensor measuring the strain in the arrangement of ultrasound units, wherein assignments between the degree of unfolding of the arrangement and the sensed strain can be provided, in order to determine the degree of unfolding of the arrangement based on the assignments and the measured strain. The ultrasound units can be operated depending on the sensed degree of unfolding of the arrangement of ultrasound units. This can lead to a further improved confinement of the ultrasound focus region such that it substantially only covers the object, but not other parts of the subject. In an embodiment the ultrasound units comprise ultrasound transducers on flexible circuits, wherein the sensor may be included in the flexible circuits.

In a further aspect of the present invention an ultrasound ablation system for a focal ablation treatment of an object within a subject is presented, wherein the ultrasound ablation system comprises:
  an ultrasound ablation device as defined in claim 1,
  an ultrasound control unit for controlling the ultrasound units such that the object is focally ablated, after the ultrasound ablation device has been inserted into the tissue such that the unfolded arrangement of ultrasound units is next to the object.

The arrangement of ultrasound units and the ultrasound control unit may be adapted to generate an ultrasound image of the object, i.e. the ultrasound units may be operable in an ablation mode and in an imaging mode. Furthermore, the ultrasound control unit may be adapted to control the ultrasound units in the ablation mode depending on the generated ultrasound image of the object. In particular, the ultrasound image can show the object to be ablated, wherein the ultrasound control unit can be adapted to control the ultrasound units in the ablation mode such that the imaged object is surely covered by the ultrasound focus region.

The ultrasound control unit can be adapted to control the ultrasound units depending on the current degree of unfolding. The ultrasound ablation device can comprise a sensor for sensing the degree of unfolding of the arrangement of ultrasound units, wherein the ultrasound control unit can be adapted to control the ultrasound units depending on the sensed degree of unfolding. The degree of unfolding can be controlled by controlling, for instance, the amount of fluid and/or the pressure within the inflatable balloon.

In a further aspect of the present invention an ultrasound ablation method for a focal ablation treatment of an object within a subject by using an ultrasound ablation system as defined in claim 10 is presented, wherein the ultrasound ablation device has been inserted into tissue surrounding the object, wherein the ultrasound ablation method comprises:
  creating space within the tissue and modifying the arrangement of ultrasound units from a folded configuration, which had been used while inserting the ultrasound ablation device into the tissue, to an unfolded configuration such that the unfolded arrangement of ultrasound units is next to the object by inflating the inflatable balloon, wherein in the unfolded configuration the ultrasound emission surfaces are directed towards the inside of the balloon, and
  controlling the ultrasound units such that the object is focally ablated by the ultrasound control unit.

In another aspect of the present invention a computer program for a focal ablation treatment of an object within a subject is presented, wherein the computer program comprises program code means for causing an ultrasound ablation system as defined in claim 10 to carry out the ultrasound ablation method determination method as defined in claim 12, when the computer program is run on the ultrasound ablation system.

It shall be understood that the ultrasound ablation device of claim 1, the ultrasound ablation system of claim 10, the ultrasound ablation method of claim 12 and the computer program of claim 13 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
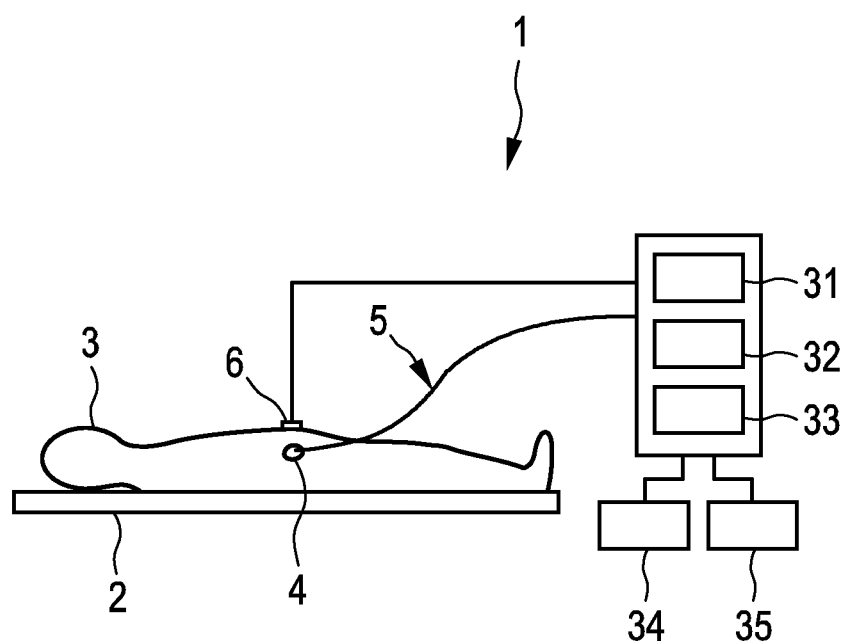
FIG. 1 shows schematically and exemplarily an embodiment of an ultrasound ablation system for a focal ablation treatment of an object within a subject.
Figure 2:
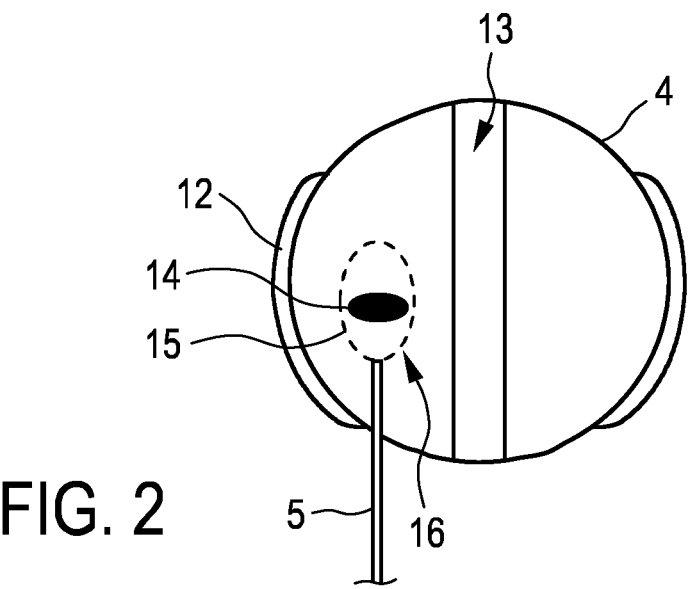
FIG. 2 illustrates schematically and exemplarily an arrangement of a forward-looking ultrasound ablation device of the ultrasound ablation system within the prostate of a person.

FIG. 1 shows schematically and exemplarily an embodiment of an ultrasound ablation system for a focal ablation treatment of an object within a subject. The ultrasound ablation system 1 comprises an ultrasound ablation device 5 being, in this embodiment, a needle device which has been inserted into the tissue of the prostate 4 of a person 3 lying on a support means 2 like a patient table. As can be seen in FIG. 2, the ultrasound ablation device 5 has been inserted into the tissue 16 of the prostate 4 such that the tip of the ultrasound ablation device 5 is close to a tumor 14 being, in this embodiment, the object to be ablated. FIG. 2 also shows nerves 12 and the urethra 13.

Figure 3:
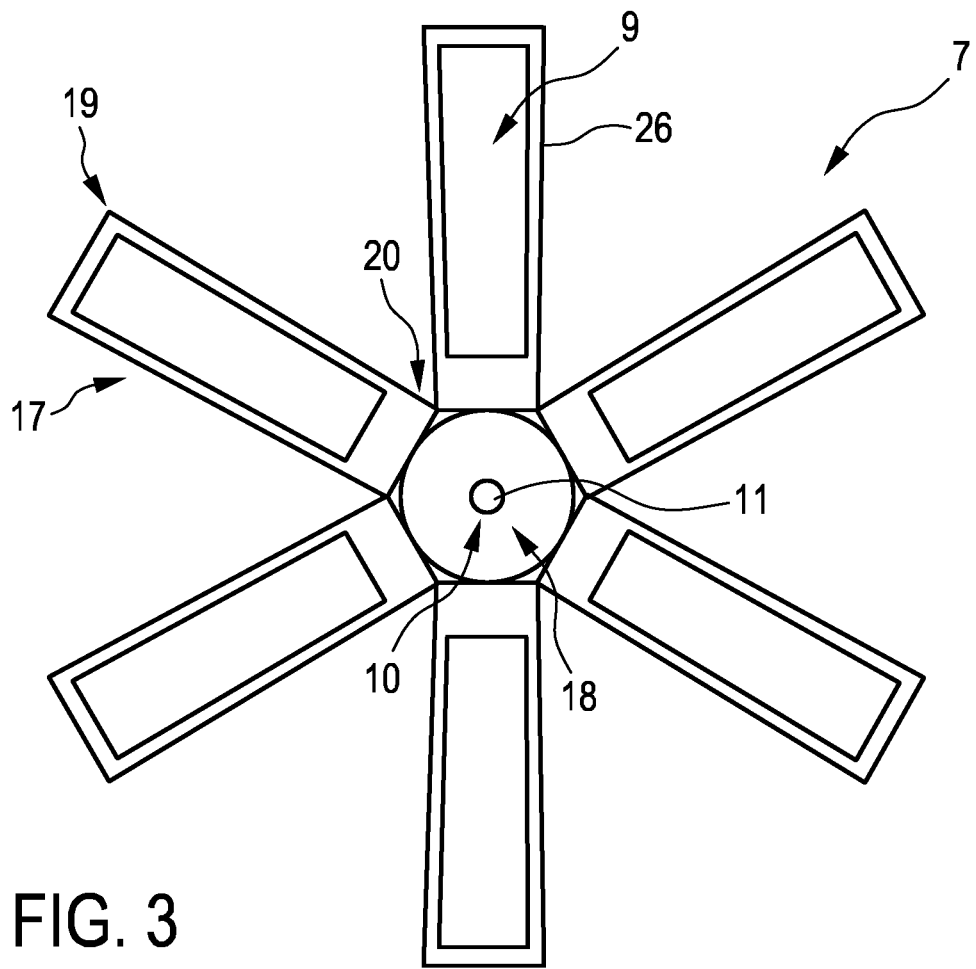
FIG. 3 shows schematically and exemplarily an embodiment of an arrangement of ultrasound transducers in an unfolded configuration.
Figure 4:
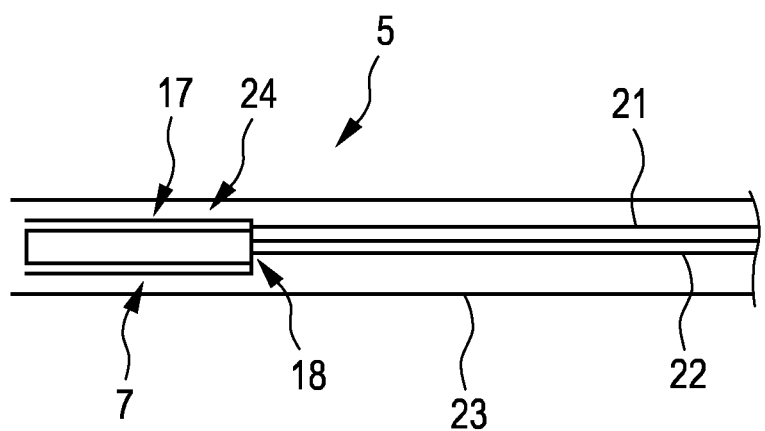
FIG. 4 shows schematically and exemplarily the embodiment of the arrangement of ultrasound units in a folded configuration.

The ultrasound ablation device 5 is an interstitial device comprising a shaft, wherein at the distal end, i.e. at the tip, of the shaft an arrangement of ultrasound units is arranged. The arrangement of ultrasound units is used for focally ablating the tumor 14, wherein an ultrasound focus region 15 is generated, which covers the tumor 14. The arrangement of ultrasound units is modifiable from a folded configuration to be used while inserting the ultrasound ablation device into the tissue 16 to an unfolded configuration to be used after the ultrasound ablation device 5 has been inserted into the tissue 16 such that the unfolded arrangement of ultrasound units is next to the tumor 14. The arrangement of ultrasound units is also modifiable from the unfolded configuration to the folded configuration, in order to easily remove the ultrasound ablation device 5 with the arrangement of ultrasound units from the person 3. FIG. 3 schematically and exemplarily shows the arrangement 7 of ultrasound units 17, 18 in its unfolded configuration, whereas FIG. 4 illustrates the arrangement 7 of ultrasound units 17, 18 in its folded configuration within the shaft 23 of the ultrasound ablation device 5. The arrangement 7 of ultrasound units 17, 18 is unfolded by using an inflatabale balloon as will be explained further below and which is not shown in FIGS. 3 and 4 for clarity reasons.

The ultrasound units include longish, rectangular elements 17 having an ultrasound emission surface 9 and a base element 18 also having an ultrasound emission surface 10. In the folded configuration illustrated in FIG. 4 the ultrasound emission surfaces 9 of different longish elements 17, i.e. of different ultrasound units, face each other, wherein the arrangement 7 of ultrasound units 17, 18 is adapted such that, while unfolding the arrangement 7 of ultrasound units 17, 18, the longish elements 17 are folded back so that first ends 19 of different longish elements 17 move away from each other and opposing second ends 20 of the different longish elements 17, which are connected to the base element 18, do not move away from each other. Thus, the unfolding of the arrangement 7 of ultrasound units 17, 18 can be regarded as corresponding to an opening of flower petals, wherein the longish elements 17 correspond to the flower petals.

The base element 18, i.e. the base ultrasound unit, has a central opening 11 for allowing a fluid to traverse the base element 18. The opening 11 of the base element 18 is connected to a tube 22 which in turn is connected to a fluid providing unit 32, in order to pump cooling fluid from the fluid providing unit 32 via the tube 22 through the opening 11. The cooling fluid may cool especially the ultrasound unit 18 and also the ultrasound units 17, when the arrangement 7 of ultrasound units 17, 18 has been unfolded and is used for ablating the tumor 14.

As can be seen in FIG. 4, the shaft 23 comprises an inner space 24 accommodating the arrangement 7 of ultrasound units 17, 18 in its folded configuration, wherein the arrangement 7 of ultrasound units 17, 18 and the inner space 24, i.e., the shaft 23, are movable relatively to each other, in order to move the arrangement 7 of ultrasound units 17, 18 out of the inner space 24 into the tissue 16 where the arrangement 7 of ultrasound units 17, 18 is unfoldable. In particular, a moving element 21 may be connected to the arrangement 7 of ultrasound units 17, 18 for moving the arrangement 7 from the inner space 24 of the shaft 23 into the tissue 16 and for moving the arrangement 7 from the tissue 16 back into the inner space 24. The moving element 21 is preferentially a wire. One end of the moving element 21 is connected to the arrangement 7 and another end of the moving element 21 is connected to an arrangement moving unit 33 which may comprise a motor for moving the moving element 21 and hence the arrangement 7.

Figure 5:
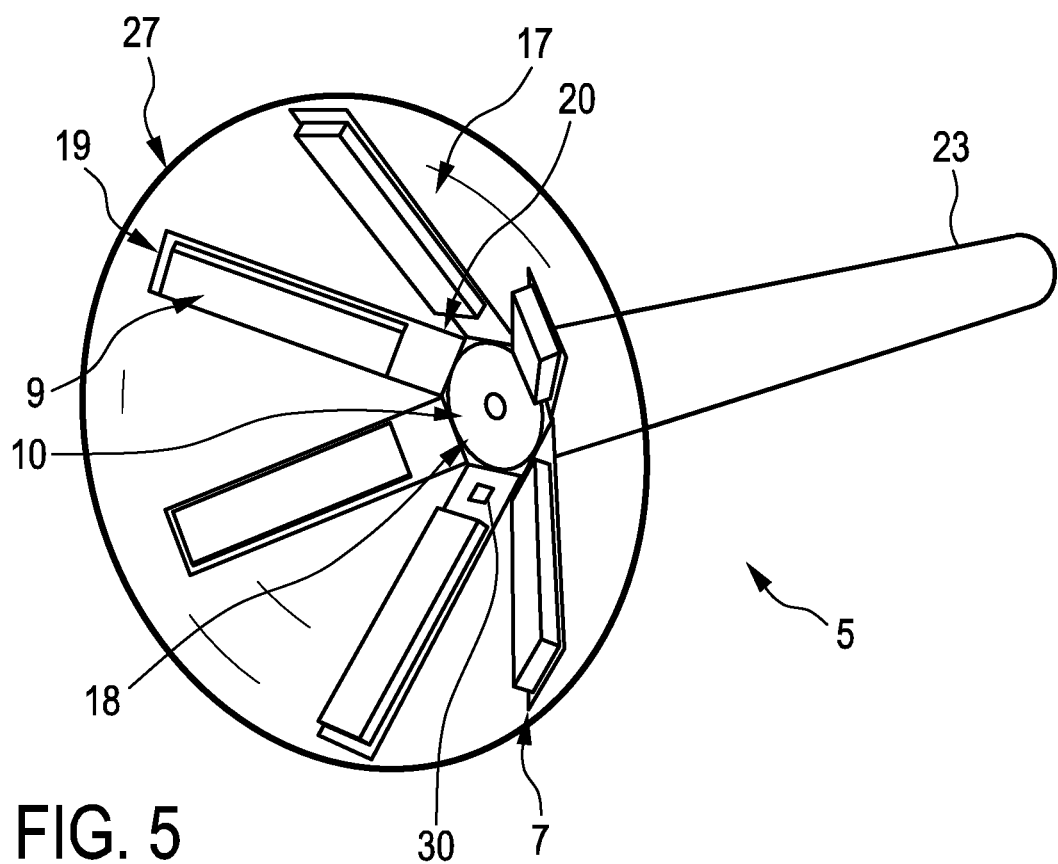
FIG. 5 shows schematically and exemplarily the embodiment of the arrangement of ultrasound units in the unfolded configuration together with an inflated balloon.

The ultrasound ablation device 5 is schematically and exemplarily shown in FIG. 5. An inflatable balloon 27 is used, wherein the arrangement 7 of ultrasound units, i.e. at least the longish ultrasound units 17 with the first and second ends 19, 20 and the ultrasound emission surface 9 and optionally also the base ultrasound unit 18 with the ultrasound emission surface 10, is located on an outer surface of the inflatable balloon 27. In this embodiment the ultrasound emission surfaces 9 face the outer surface of the inflatable balloon 27. In another embodiment the ultrasound units might be located on the inner surface of the balloon 27 such that non-ultrasound-emission surfaces of the ultrasound transducers, which are opposite to the ultrasound emission surfaces, face the inner surface of the inflatable balloon.

The arrangement 7 of the ultrasound units 17, 18 is modified from the folded configuration to the unfolded configuration by inflating the balloon 27. This inflation of the balloon 27 is preferentially carried out by providing fluid through the central opening of the base element 18 of the arrangement 17 by using the fluid providing unit 32. In another embodiment the fluid may be provided to the balloon 27 in another way, particularly if in another embodiment the arrangement of ultrasound units does not comprise a base element with a central opening.

The fluid for inflating the balloon 27 is preferentially cooling fluid which does not only cool the ultrasound units, but which also filters the ultrasound near field. For deflating the balloon 27 the fluid providing unit 32 may be adapted to pump the fluid out of the balloon 27. Alternatively or in addition, for deflating the balloon 27 the balloon 27 may comprise a further opening allowing the fluid to leave the balloon 27, wherein in this case the balloon 27 may be deflated by reducing the flow of fluid into the balloon 27, particularly by stopping the flow of fluid into the balloon 27.

The arrangement 107 of ultrasound units 17, 18 and the balloon 27 are adapted to generate an ultrasound focus region outside the balloon 27, if the balloon 27 is completely inflated. The arrangement 7 is located at the distal tip of the shaft 23 of the ultrasound ablation device 5, wherein the shaft 23 comprises the inner space in which the arrangement 7 is located in its folded configuration, if the shaft 23 is inserted into the tissue 16. After having been inserted into the tissue 16 the arrangement 7 is moved out of the shaft 23 and the balloon 27 is inflated, in order to unfold the arrangement 7.

The arrangement 7 of ultrasound units 17, 18 is preferentially rotatable relative to the shaft 23. This allows for a rotational positioning of the ultrasound focus region without rotating the shaft, which can lead to an improved handling of the ultrasound ablation device.

The embodiment of the ultrasound ablation device described above with reference to FIGS. 2 to 5 comprises an arrangement of ultrasound units being forward-looking. However, in another embodiment the arrangement of ultrasound units can also be sideward-looking. Also in this case the ultrasound units are located on a surface of an inflatable balloon such that the ulrasound emission surfaces are directed towards the inside of the balloon and the arrangement is unfolded by inflating the balloon.

Figure 6:
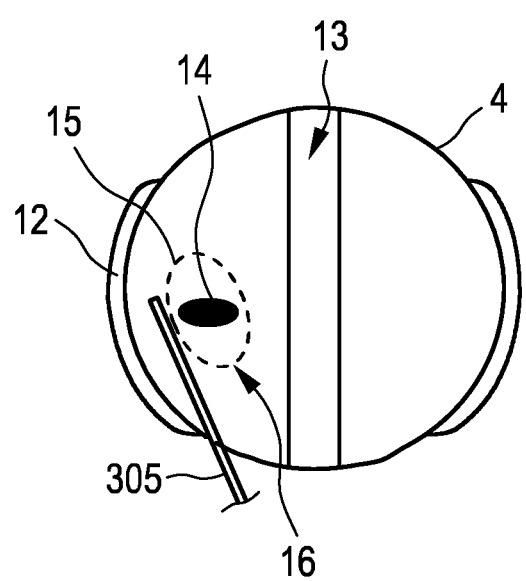
FIG. 6 illustrates schematically and exemplarily an arrangement of a sideward-looking ultrasound ablation device within the prostate of the person.

FIG. 6 schematically and exemplarily illustrates an ultrasound ablation device 305 with a sideward-looking arrangement within the prostate 4. The ultrasound focus region 15 is located at a side of the tip of the ultrasound ablation device 305 and covers the tumor 14 for ablating the same.

Referring again to FIG. 1, the ultrasound ablation system 1 further comprises an ultrasound control unit 31 for controlling the ultrasound units such that the tumor 14 is focally ablated, after the ultrasound ablation device has been inserted into the tissue 16 such that the unfolded arrangement of ultrasound units is next to the object. In particular, the ultrasound control unit 31 is preferentially adapted to electronically steer and focus the ultrasound beam such that the tumor 14 is focally ablated. This allows for a modification of the location and/or shape and/or dimensions of the ultrasound focus region without necessarily requiring a change of the position of the ultrasound ablation device. The location and/or shape and/or dimensions of the ultrasound focus region can be particularly well modified, if the ultrasound units comprise CMUTs, because CMUTs have a relatively broad frequency bandwidth that allows for relatively large changes of the location and/or shape and/or dimensions of the ultrasound focus region by changing the frequency of the CMUTs. The ultrasound control unit 31 can comprise at least one application-specific integrated circuit (ASIC) for performing this task. The arrangement of ultrasound units and the ultrasound control unit 31 may also be adapted to generate an ultrasound image of the tumor 14, i.e. the ultrasound units may be operable in an imaging mode and in an ablation mode. The ultrasound control unit 31 may be adapted to control the ultrasound units in the ablation mode depending on the generated ultrasound image of the tumor 14 such that the ultrasound focus region 15 surely covers the tumor 14.

The ultrasound ablation system 1 comprises an additional ultrasound imaging device 6 placed on the outer surface of the person 3. The ultrasound imaging device 6 is used together with the ultrasound control unit 31 for generating an ultrasound image showing the prostate 4 with the tumor 14 and the tip of the ultrasound ablation device while being inserted into the tissue 16 of the prostate 4. This ultrasound image can be used as a guide while navigating the ultrasound ablation device within the person 3. In another embodiment also another kind of ultrasound imaging device can be used. For instance, a transrectal ultrasound imaging (TRUS) device can be used for generating an image showing the prostate, the tumor, the ultrasound ablation device and also further elements like the nerves, urethra, et cetera.

The ultrasound ablation system 1 comprises a display 35 for displaying at least the image and an input unit 34 like a keyboard, a computer mouse, a touch pad et cetera, in order to allow a user to input, for instance, commands or parameters into the ultrasound ablation system 1. For instance, a start command for starting an image generation process or for starting an ablation process may be input via the input unit 34. Also a corresponding stop command may be input via the input unit 34.

The ultrasound ablation device may comprise a sensor for sensing the degree of unfolding of the arrangement of ultrasound units. Such a sensor is schematically and exemplarily indicated in FIG. 5 by the box 30. Preferentially the ultrasound units comprise ultrasound transducers on flexible circuits, wherein in an embodiment this sensor 30 is a strain sensor for measuring the strain within the flexible circuits and wherein the measured strain is provided to the ultrasound control unit 31. The ultrasound control unit 31 comprises assignments between the measured strain and the degree of unfolding of the arrangement of the ultrasound units, which allows the ultrasound control unit 31 to determine the degree of unfolding of the arrangement based on the measured strain. This information can be used by the ultrasound control unit 31 for controlling the ultrasound units depending on the current degree of unfolding.

Figure 7:
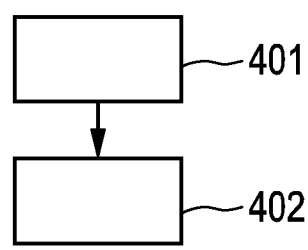
FIG. 7 shows a flowchart exemplarily illustrating an embodiment of an ultrasound ablation method for a focal ablation treatment of an object within a subject.

In the following an embodiment of an ultrasound ablation method for a focal ablation treatment of an object within a subject will be exemplarily described by reference to a flowchart shown in FIG. 7.

The ultrasound ablation device has already been inserted into tissue surrounding the object, while the arrangement of ultrasound units was in its folded configuration. In step 401 the arrangement of the ultrasound units is modified from the folded configuration to the unfolded configuration such that the unfolded arrangement of ultrasound units is next to the object. In step 402 the ultrasound units are controlled by the ultrasound control unit such that the object is focally ablated, i.e. such that the object is covered by the ultrasound focus region.

An ultrasound-based focal ablation treatment is a treatment in which an ultrasound focus region is generated, which covers the object to be ablated. The benefit of the focal treatment is the preservation of the uninvolved surrounded healthy tissue like the sphincters, neurovascular bundles and normal prostate gland. The ultrasound-based focal ablation treatment technique is preferentially a minimally invasive technique. The ultrasound-based focal ablation treatment may be carried out one time or several times for treating a same object, especially a same tumor. The above described ultrasound ablation devices, which are preferentially ultrasound ablation needle devices, can precisely treat tumors even in the peripheral zone of the prostate and minimize side effects. In order to reach relatively large acoustic power levels and corresponding beam profiles for ultrasound ablation, the unfolded arrangement of ultrasound units provides a relatively large active ultrasound transducer area having dimensions, especially dimensions of lengths of the sides of the ultrasound transducer area, that are larger than the outer diameter of current ablation needle devices, which might be about 1 mm. The outer diameter of the current ablation needle devices of, for instance, about 1 mm should not be increased, because increasing the outer diameter would lead to patient discomfort and makes percutaneous interventions more invasive.

The ultrasound ablation device can comprise ultrasound transducers like CMUTs, flexible electronics and an inflatable balloon to create a foldable arrangement of ultrasound units. This arrangement of ultrasound units can fit within a needle, an additional sheath or another element. At the desired location the arrangement of ultrasound units can unfold like the opening of flower petals for optimal therapy delivery. The arrangement of ultrasound transducers can be folded in again, when the ultrasound ablation device, in particular, the ultrasound ablation needle device, is retrieved from the body. In this way an interstitial ultrasound ablation device can be provided with an enlarged ultrasound transducer area. In addition this ultrasound therapy allows for tumor ablation without directly inserting the ultrasound ablation device into a tumor which prevents tumor seeding after needle retraction.

The ultrasound transducers of the ultrasound units may be CMUTs which may be manufactured using silicon IC technology. The ultrasound units may be connected to each other via the flexible circuits, i.e., for instance, referring to FIGS. 3 to 5, the longish elements 17 may be connected to the base elements 18 via the flexible circuits. The design of the ultrasound units can be identical for all ultrasound units or different to create the most optimal ultrasound beam profile, wherein the design may refer to a membrane diameter or a stack design.

During insertion of the interstitial device into the body the leave-like arrangement of ultrasound units will be folded inward and the complete arrangement of ultrasound units is housed within the interstitial device, especially within an interstitial needle or an additional sheath. To allow free deployment of the leave-like arrangement of ultrasound units a sheath could be pulled backwards or the arrangement of ultrasound units could be pushed forward at the desired location within the body.

As explained above with reference to FIG. 5, an inflated, especially, a water-filled, balloon could enable the opening of the ultrasound units. Such a balloon can be used to free-up space within dense tissue to assist in deploying the arrangement of ultrasound units. Water cooling can furthermore be used to cool the ultrasound transducers as well as to filter the ultrasound near field. The hole in the center of the round base element allows the inflow and outflow of cool water. The ultrasound focus is located outside of the balloon. The position of the ultrasound focus can be adapted by changing the operating frequency. In this way the ultrasound energy can be deposited at the desired location within the tissue.

The ultrasound transducers can be adapted to operate in a frequency range of, for instance, 1 to 10 MHz or 1 to 25 MHz. They can be driven with a continuous sine wave. However, the ultrasound transducers can of course also be operated in another way such that the acoustic power in the ultrasound focus region is sufficient for tissue ablation. The ultrasound transducers can be driven either simultaneously or individually. The design of the ultrasound units, for instance, the membrane diameter of the ultrasound transducers or the design of the stack of the different elements of the ultrasound units, can either be identical for all corresponding ultrasound units, i.e., for instance, for all leave-like ultrasound units described above with reference to FIGS. 3 to 5, or the design can be different to create the most optimal ultrasound beam profile.

Although in above described embodiments the ultrasound ablation device is preferentially an ultrasound ablation needle device, in other embodiments the ultrasound ablation device can also be another minimally invasive device like a catheter or an endoscope, i.e. a catheter or an endoscope may be equipped with the foldable arrangement of ultrasound units for focally ablating an object. Also a surgical element like a grasper, a clamp, a retractor, et cetera may be equipped with the foldable arrangement of ultrasound units for focally ablating an object.

Moreover, although in above described embodiments the ultrasound ablation device is mainly used to ablate a tumor in the prostate, the ultrasound ablation device can also be used to target other objects in other parts of a subject like the liver. The ultrasound therapy can be combined with ultrasound imaging in a single device for optimal therapy control, wherein the ultrasound imaging may be used for thermometry and/or elastography and wherein the ultrasound therapy, i.e. the ultrasound units of the unfolded arrangement, may be controlled depending on this information. Sensors may be included in the flexible components of the ultrasound units like the flexible circuits for determining, for instance, the degree of deployment of the arrangement of ultrasound units or the temperature increase in the tissue. Also this information may be used for controlling the ultrasound ablation.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

Procedures like the determination of the degree of unfolding of the arrangement of ultrasound transducers performed by one or several units or devices can be performed by any other number of units or devices. These procedures and/or the control of the ultrasound ablation system in accordance with the ultrasound ablation method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an interstitial ultrasound ablation device for being inserted into tissue surrounding, for instance, a tumor. The interstitial ultrasound ablation device comprises an arrangement of ultrasound units for a focal ablation treatment which is modifiable from a folded configuration, to be used while inserting the ultrasound ablation device into the tissue, to an unfolded configuration, to be used after the ultrasound ablation device has been inserted into the tissue, such that the unfolded arrangement of ultrasound units is next to the tumor. This ultrasound ablation device can be easily positioned close to the tumor, where the unfolded arrangement of ultrasound units provides a large ultrasound emission area allowing for a very good focusing of the ultrasound on the tumor. This can lead to a very effective ablation of the tumor with only very few or no unwanted side effects.

The invention claimed is:

1. An ultrasound ablation device for a focal ablation treatment of an object within a subject, wherein the ultrasound ablation device is an interstitial device to be inserted into tissue surrounding the object and comprises an arrangement of ultrasound units for focally ablating the object by ultrasound, wherein the arrangement of ultrasound units is modifiable from a folded configuration, to be used while inserting the ultrasound ablation device into the tissue, to an unfolded configuration, to be used after the ultrasound ablation device has been inserted into the tissue, such that the unfolded arrangement of ultrasound units is next to the object, wherein the ultrasound ablation device comprises an inflatable balloon for creating space within the tissue by inflating the balloon, wherein each ultrasound unit comprises an ultrasound emission surface, wherein the arrangement of ultrasound units is located on a surface of the inflatable balloon such that in the unfolded configuration the ultrasound emission surfaces are directed towards the inside of the balloon.

2. The ultrasound ablation device as defined in claim 1, wherein the arrangement of ultrasound units is located on an outer surface of the inflatable balloon such that the ultrasound emission surfaces face the outer surface of the inflatable balloon.

3. The ultrasound ablation device as defined in claim 1, wherein each ultrasound unit comprises a respective non-ultrasound-emission surface being opposite to the respective ultrasound emission surface, wherein the arrangement of ultrasound units is located on an inner surface of the inflatable balloon such that the non-ultrasound-emission surfaces face the inner surface of the inflatable balloon.

4. The ultrasound ablation device as defined in claim 1, wherein the arrangement of ultrasound units is adapted such that in the folded configuration the ultrasound emission surfaces of at least some ultrasound units face each other and that, while unfolding the arrangement of ultrasound units, these ultrasound units are folded back so that first ends of these ultrasound units move away from each other and opposing second ends of these ultrasound units do not move away from each other.

5. The ultrasound ablation device as defined in claim 4, wherein the ultrasound units include a base ultrasound unit having an ultrasound emission surface and being surrounded by the second ends of the ultrasound units that are folded back while unfolding the arrangement.

6. The ultrasound ablation device as defined in claim 5, wherein the base ultrasound unit has an opening for allowing a fluid to traverse the base ultrasound unit.

7. The ultrasound ablation device as defined in claim 1, wherein the ultrasound ablation device comprises an inner space for accommodating the arrangement of ultrasound units in its folded configuration, wherein the arrangement of ultrasound units and the inner space are movable relatively to each other for moving the arrangement of ultrasound units out of the inner space into tissue where the arrangement of ultrasound units is unfoldable.

8. The ultrasound ablation device as defined in claim 1, wherein the ultrasound ablation device comprises a shaft to be inserted into the tissue surrounding the object, wherein the arrangement of ultrasound units surrounds the shaft in its folded configuration.

9. The ultrasound ablation device as defined in claim 1, wherein the ultrasound ablation device comprises a sensor for sensing the degree of unfolding of the arrangement of ultrasound units.

10. An ultrasound ablation system for a focal ablation treatment of an object within a subject, wherein the ultrasound ablation system comprises:
an ultrasound ablation device as defined in claim 1,
an ultrasound control unit for controlling the ultrasound units such that the object is focally ablated, after the ultrasound ablation device has been inserted into the tissue such that the unfolded arrangement of ultrasound units is next to the object.

11. The ultrasound ablation system as defined in claim 10, wherein the arrangement of ultrasound units is unfoldable to different degrees of unfolding in its unfolded configuration and the ultrasound control unit is adapted to control the ultrasound units depending on the current degree of unfolding.

12. An ultrasound ablation method for a focal ablation treatment of an object within a subject by using an ultrasound ablation system as defined in claim 10, wherein the ultrasound ablation device has been inserted into tissue surrounding the object, wherein the ultrasound ablation method comprises:
creating space within the tissue and modifying the arrangement of ultrasound units from a folded configuration, which had been used while inserting the ultrasound ablation device into the tissue, to an unfolded configuration such that the unfolded arrangement of ultrasound units is next to the object by inflating the inflatable balloon, wherein in the unfolded configuration the ultrasound emission surfaces are directed towards the inside of the balloon, and
controlling the ultrasound units such that the object is focally ablated by the ultrasound control unit.

* * * * *